United States Patent
Chassot et al.

(10) Patent No.: US 6,936,077 B2
(45) Date of Patent: Aug. 30, 2005

(54) 1,3-DIAMINO-4-(AMINOMETHYL)—BENZENE DERIVATIVES AND COLORANTS CONTAINING THE SAID COMPOUNDS

(75) Inventors: Laurent Chassot, Praroman (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 272 days.

(21) Appl. No.: 10/276,567
(22) PCT Filed: Oct. 19, 2001
(86) PCT No.: PCT/EP01/12124
§ 371 (c)(1), (2), (4) Date: Nov. 14, 2002
(87) PCT Pub. No.: WO02/076923
PCT Pub. Date: Oct. 3, 2002

(65) Prior Publication Data
US 2003/0172471 A1 Sep. 18, 2003

(30) Foreign Application Priority Data
Mar. 22, 2001 (DE) .......... 101 14 084

(51) Int. Cl.⁷ .............. A61K 7/13
(52) U.S. Cl. ........ 8/405; 8/406; 8/409; 8/411; 8/423; 564/306; 564/307
(58) Field of Search .......... 8/405, 406, 409, 8/411, 423; 564/306, 307

(56) References Cited

U.S. PATENT DOCUMENTS 3,743,509 A 7/1973 Baltazzi .......... 96/91
5,968,206 A * 10/1999 Audousset et al. ........ 8/409

FOREIGN PATENT DOCUMENTS

| DE | 35 08 309 A1 | 9/1986 |
| DE | 38 24 299 A | 4/1990 |
| DE | 199 61 274 C | 2/2001 |
| DE | 199 61 229 C | 4/2001 |
| EP | 0 398 702 A | 11/1990 |
| EP | 0740 931 A1 | 11/1996 |
| WO | WO 90/01022 * | 2/1990 ............ A61K/7/13 |

OTHER PUBLICATIONS

Database Registry "Online" Chemical Abstracts Service, Columbus, OH, US, RN =100911–46–4, XP002191662. 1967.

* cited by examiner

Primary Examiner—Margaret Einsmann
Assistant Examiner—Eisa Elhilo
(74) Attorney, Agent, or Firm—Michael J. Striker

(57) ABSTRACT

1,3-Diamino-4-(aminomethyl)-benzene derivatives of the general Formula (I) or their physiologically tolerated, water-soluble salts,

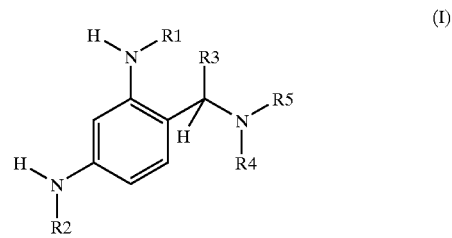

as well as agents for the oxidative dyeing of fibers, containing these compounds.

12 Claims, No Drawings

1,3-DIAMINO-4-(AMINOMETHYL)—BENZENE DERIVATIVES AND COLORANTS CONTAINING THE SAID COMPOUNDS

BACKGROUND OF THE INVENTION

1. Field of the Invention

The invention relates to the new 1,3-diamino-4-(aminomethyl)-benzene derivatives, as well as to agents containing these compounds, for dyeing keratin fibers.

2. Description of Related Art

In the field of dyeing keratin fibers, especially of dyeing hair, oxidation dyes have achieved a significant importance. The dyeing is brought about here by the reaction of certain developer substances with certain coupler substances in the presence of a suitable oxidizing agent. As developer substances, 2,5-diaminotoluene, 2,5-diaminophenylethyl alcohol, p-aminophenol, 1,4-diaminobenzene and 4,5-diaminopyrazole-1-(2-hydroxyethyl) and, as coupler substances, resorcinol, 2-methyl-resorcinol, 1-naphthol, 3-aminophenol, m-phenylene-diamine, 2-amino-4-(2'-hydroxyethyl)amino-anisole, 1,3-diamino-4-(2'-hydroxyethoxy)benzene and 2,4-diamino-5-fluoro-toluene, for example, are named here.

Oxidation dyes, which are used to dye human hair, must meet numerous requirements in addition to dyeing the hair in the desired intensity. For example, the dyes must be safe from toxicological and dermatological points of view the dyeings achieved must exhibit good light fastness, permanent waving fastness, acid fastness and crocking fastness. In any case, however, such dyeings must remain stable over a period of at least 4 to 6 weeks without the action of light, rubbing and chemical agents. In addition, it is necessary that a broad range of different color nuances can be produced by combinations of suitable developer substances and coupler substances.

An attempt has already been made to improve the properties of m-phenylenediamines by the introduction of substituents. In this connection, reference is made to the German Offenlegungsschriften 35 08 309 and 38 24 299, from which the use of 5-substituted m-phenylenediamines in oxidation hair-dyeing agents is known. Moreover, from the EP OS 0 740 931, the use of 1-substituted m-phenylenediamines in oxidation hair-dyeing agents is known. However, with the dyeing agents known at the present time, it is not possible to fulfill the requirements, which must be met by a dyeing agent, in all respects. For this reason, there continues to be a need for new developer substances, which fulfill the above-mentioned requirements particularly well.

SUMMARY OF THE INVENTION

It has now been found that, if 1,3-diamino-4-(aminomethyl)-benzene derivatives of the general Formula (I) are used, intensive, stable, blue color nuances are obtained.

An object of the present invention therefore are 1,3-diamino-4-(aminomethyl)-benzene derivatives of the general Formula (I) or their physiologically tolerated, water-soluble salts,

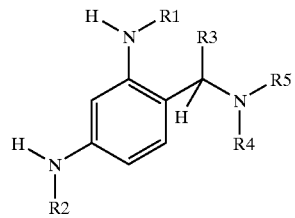

wherein
R1 and R2 independently of one another are hydrogen, a $C_1$–$C_6$ alkyl group, a $C_2$–$C_4$ hydroxyalkyl group or a $C_3$–$C_4$ dihydroxyalkyl group,
R3 is hydrogen or a $C_1$–$C_4$ alkyl group,
R4 and R5 independently of one another are hydrogen, a $C_1$–$C_2$ alkoxy group, a saturated $C_1$–$C_6$ alkyl group, an unsaturated $C_3$–$C_6$ alkyl group, a $C_2$–$C_4$ hydroxyalkyl group, a $C_3$–$C_4$ dihydroxyalkyl group, a $C_2$–$C_4$ aminoalkyl group, a $C_2$–$C_4$ dimethylaminoalkyl group, a $C_2$–$C_4$ acetylaminoalkyl group, a $C_2$–$C_4$ methoxyalkyl group, a $C_2$–$C_4$ ethoxyalkyl group, a $C_1$–$C_4$ cyanoalkyl group, a $C_1$–$C_4$ carboxyalkyl group, a $C_1$–$C_4$ aminocarbonylalkyl group, a pyridylmethyl group, a furfuryl group, a thienyl methyl group, a substituted pyridyl group or a group of Formula (II)

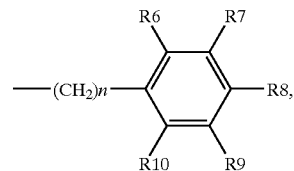

or R4 and R5 together with the nitrogen atom form a ring of Formula

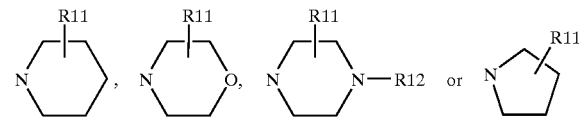

R6, R7, R8, R9 and R10 independently of one another represent hydrogen, a halogen atom (F, Cl, Br, I), a cyano group, a hydroxy group, a $C_1$–$C_4$ alkoxy group, a $C_2$–$C_4$ hydroxyalkoxy group, a $C_1$–$C_6$ alkyl group, a $C_1$–$C_4$ alkyl thioether group, a mercapto group, a nitro group, an amino group, an alkylamino group, a di($C_1$–$C_6$ alkyl) amino group, a dihydroxy-($C_3$–$C_4$)alkyl)amino group, a di($C_1$–$C_4$ hydroxyalkyl)amino group, a ($C_1$–$C_4$ hydroxyalkyl)-($C_1$–$C_6$ alkyl)-amino group, a trifluoromethane group, a —C(O)H group, a —C(O)$CH_3$ group, a —C(O)$CF_3$ group, an —Si($CH_3$)$_3$ group, a $C_1$–$C_4$ hydroxyalkyl group, a $C_2$–$C_4$ dihydroxyalkyl group, a carboxy group or a pyrrolidine group or two R6 to R10 groups, adjacent to one another, form an —O—CH2-O link,
R11 is hydrogen, a hydroxy group, a carboxy group, an aminocarbonyl group or a hydroxymethyl group;
R12 is hydrogen or a $C_1$–$C_6$ alkyl group; and
n is 0 or 1.

As suitable compounds of Formula (I), the following compounds, for example, may be named: 1,3-diamino-4-(methylamino-methyl)-benzene, 1,3-diamino-(4- allylaminomethyl)-benzene, 2-(2,4-diamino-benzylamino)-ethanol, 1,3-diamino-4-(pyrrolidine-1-ylmethyl)-benzene, 1-(2,4-diamino-benzyl)-pyrrolidine-3-ol, [1-(2,4-diaminobenzyl)-pyrrolidine-2-yl]-methanol, 1,3-diamino-4-[(2-aminoethylamino)-methyl]-benzene, 1,3-diamino-4-morpholine-4-ylmethyl-benzene, 1-(2,4-diaminobenzyl)-piperidine-4-ol, 1-(2,4-diaminobenzyl)-piperidine-3-ol, N-[2-(2,4-diamino-benzylamino)-ethyl]-acetamide, 3-[2-(2,4-diaminobenzylamino)-1-hydroxyethyl]-phenol, 1,3-diamino-4-[(2-methoxyethylamino)-methyl]-benzene, 2-(2,4-diaminobenzylamino)-propane-1-ol, 1,3-diamino-4-{[(tetrahydrofuran-2-ylmethyl)-amino]-methyl}-benzene, 1,3-diamino-4-((2-aminophenylamino)-methyl)-benzene, 1,3-diamino-4-((3-aminophenyl-amino)-methyl)-benzene, 1,3-diamino-4-((2-hydroxyphenylamino)-methyl)-benzene, 1,3-diamino-4-((3-hydroxyphenylamino)-methyl)-benzene, 1,3-diamino-4-((2-hydroxyphenylamino)-methyl)-benzene, 1,3-diamino-4-((4-hydroxyphenylamino)-methyl)-benzene and 1,3-diamino-4-((4-methyl-phenylamino)-methyl)-benzene.

Compounds of Formula (I), in which (i) one or more or all of the R1, R2 and R3 groups are hydrogen and/or (ii) one of the R4 or R5 groups is a $C_2$–$C_4$ hydroxyalkyl group, an unsaturated $C_3$–$C_6$ alkyl group, a $C_2$–$C_4$ aminoalkyl group or a $C_1$–$C_4$ alkyl group, are preferred.

Especially the following compounds of Formula (I) are preferred: 1,3-diamino-4-(methylaminomethyl)-benzene, 1,3-diamino-(4-allyl-aminomethyl-benzene, 2-(2,4-diaminobenzylamino)-ethanol and 1,3-diamino-4-[(2-aminoethylamino)-methyl]-benzene.

The 1,3-diamino-4-(aminomethyl)-benzene derivatives of Formula (I) can be used as free bases as well as in the form of their physiologically tolerated salts with inorganic or organic acids such as hydrochloric acid, sulfuric acid, phosphoric acid, acetic acid, propionic acid, lactic acid or citric acid.

The inventive diaminobenzene derivatives of Formula (I) can be synthesized using known methods. For example, the synthesis of the inventive compounds can be carried out as follows:

a reductive amination of a substituted benzene of Formula (III with an amine having the formula NHR4R5

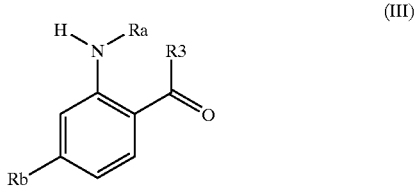

the protective group being split off subsequently,
in which
Ra represents a protective group, such as those described in the chapter "Protective Groups" in Organic Synthesis, chapter 7, Wiley Interscience, 1991,
Rb represents NR2Ra and
R2, R3, R4 and R5 have the meanings given in Formula (I).

The inventive 1,3-diamino-4-(aminomethyl)-benzene derivatives of Formula (I) are readily soluble in water and make dyeings possible with a high color intensity and an excellent color fastness, especially as far as the light fastness, washing fastness and crocking fastness are concerned. The compounds of Formula (I) furthermore have an excellent shelf life, especially as a component of the dyeing agent described below.

Agents for the oxidative dyeing of keratin fibers, such as hair, fur, feathers or wool, especially of human hair, based on a combination of a developer substance and a coupler substance, which contain at least one 1,3-diamino-4-(aminomethyl) benzene derivatives of Formula (I), are therefore a further object of the present invention.

The 1,3-diamino 4-(aminomethyl)-benzene derivatives of Formula (I) are contained in the inventive dyeing agent in an amount of about 0.005 to 20 percent by weight, an amount of about 0.01 to 5.0 percent by weight and especially of 0.1 to 2.5 percent by weight being preferred.

As developer substances, preferably 1,4-diamino-benzene (p-phenylenediamine), 1,4-diamino-2-methyl-benzene (p-toluylenediamine), 1,4-diamino-2,6-dimethyl-benzene, 1,4-diamino-3,5-diethyl-benzene, 1,4-diamino-2,5-dimethyl-benzene, 1,4-diamino-2,3-dimethyl-benzene, 2-chloro-1,4-diaminobenzene, 1,4-diamino-2-(thiophene-2-yl)-benzene, 1,4-diamino-2-(thiophene-3-yl)-benzene, 1,4-diamino-2-(pyridine-3-yl)-benzene, 2,5-diaminobiphenyl, 1,4-diamino-2-methoxymethyl-benzene, 1,4-diamino-2-aminomethyl-benzene, 1,4-diamino-2-hydroxymethyl-benzene, 1,4-diamino-2-(2-hydroxyethoxy)-benzene, 2-(2-acetylamino)ethoxy)-1,4-diaminobenzene, 4-phenylamino-aniline, 4-dimethylamino-aniline, 4-diethylamino-aniline, 4-dipropylamino-aniline, 4-[ethyl(2-hydroxyethyl)-amino]-aniline, 4-[di(2-hydroxyethyl)amino]-aniline, 4-[di(2-hydroxyethyl)-amino]-2-methyl-aniline, 4-[(2-methoxyethyl)amino]-aniline, 4-[(3-hydroxy-propyl)amino]-aniline, 4-[(2,3-dihydroxypropyl)amino]-aniline, 1,4-diamino-2-(1-hydroxyethyl)-benzene, 1,4-diamino-2-(2-hydroxyethyl)-benzene, 1,4-diamino-2-(1-methylethyl)-benzene, 1,3-bis[(4-aminophenyl)(2-hydroxyethyl)amino]-2-propanol, 1,4-bis[(4-aminophenyl)amino]-butane, 1,8-bis(2,5-diaminophenoxy)-3,6-dioxaoctane, 4-amino-phenol, 4-amino-3-methyl-phenol, 4-amino-3-(hydroxymethyl)-phenol, 4-amino-3-fluoro-phenol, 4-methylamino-phenol, 4-amino-2-(aminomethyl)-phenol, 4-amino-2-(hydroxymethyl)-phenol, 4-amino-2-fluoro-phenol, 4-amino-2-[(2-hydroxyethyl)-amino]methyl-phenol, 4-amino-2-methyl-phenol, 4-amino-2-(methoxymethyl)-phenol, 4-amino-2-(2-hydroxyethyl)-phenol, 5-amino-salicylic acid, 2,5-diamino-pyridine, 2,4,5,6-tetraamino-pyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-amino-phenol, 2-amino-6-methyl-phenol, 2-amino-5-methyl-phenol and 1,2,4-trihydroxy-benzene come into consideration.

Furthermore, in addition to the compounds of Formula (I), the inventive dyeing agent may contain further, known, coupler substances, such as N-(3-dimethylamino-phenyl)-urea, 2,6-diamino-pyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxy-benzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxy-pyridine, 1,3-diaminobenzene, 2,4-diamino-1-(2-hydroxyethoxy)-benzene, 1,3-diamino-4-(2,3-dihydroxypropoxy)-benzene, 1,3-diamino-4-(3-hydroxypropoxy)-benzene, 1,3-diamino-4-(2-methoxyethoxy)-benzene, 2,4-diamino-1,5-di(2-hydroxyethoxy)-benzene, 1-(2-aminoethoxy)-2,4-diaminobenzene, 2-amino-1-(2-hydroxyethoxy)-4-methylamino-benzene, 2,4-diamino-phenoxyacetic acid, 3-[di(2-hydroxyethyl)amino]-aniline, 4-amino-2-di[(2-hydroxyethyl)amino]-1-ethoxy-benzene, 5-methyl-2-(1-methylethyl)-phenol, 3-[(2-hydroxyethyl)amino]-aniline, 3-[(2-aminoethyl)amino]-aniline, 1,3-di(2,4-diaminophenoxy)-propane, di(2,4-diaminophenoxy)-methane, 1,3-diamino-2,4-dimethoxy-benzene, 2,6-bis(2-hydroxyethyl)amino-toluene, 4-hydroxyindole, 3-dimethylamino-phenol, 3-diethylamino-phenol, 5-amino-2-methyl-phenol, 5-amino-4-fluoro-2-methyl-phenol, 5-amino-4-methoxy-2-methyl-phenol, 5-amino-4-ethoxy-2-methyl-phenol, 3-amino-2,4-dichlorophenol, 5-amino-2,4-dichlorophenol, 3-amino-2-methyl-phenol, 3-amino-2-chloro-6-methyl-phenol, 3-aminophenol, 2-[(3-hydroxyphenyl)-amino]-acetamide, 5-[(2-hydroxyethyl)amino]-4-methoxy-2-methyl-phenol, 5-[(2-hydroxyethyl)amino]-2-methyl-phenol, 3-[(2-hydroxyethyl)amino]-phenol, 3-[(2-methoxyethyl)amino]-phenol, 5-amino-2-ethyl-phenol, 5-amino-2-methoxy-phenol, 2-(4-amino-2-hydroxyphenoxy)-ethanol, 5-[(3-hydroxypropyl)amino]-2-methyl-phenol, 3-[(2,3-dihydroxypropyl)-amino]-2-methyl-phenol, 3-[(2-hydroxyethyl)amino]-2-methyl-phenol, 2-amino-3-hydroxy-pyridine, 2,6-dihydroxy-3,4-dimethyl-pyridine, 5-amino-4-chloro-2-methyl-phenol, 1-naphthol, 2-methyl-1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol acetate, 1,3-dihydroxy-benzene, 1-chloro-2,4-dihydroxy-benzene, 2-chloro-1,3-dihydroxy-benzene, 1,2-dichloro-3,5-dihydroxy-4-methylbenzene, 1,5-dichloro-2,4-dihydroxy-benzene, 1,3-dihydroxy-2-methylbenzene, 3,4-methylenedioxy-phenol, 3,4-methylenedioxy-aniline, 5-[(2-hydroxyethyl)amino]-1,3-benzodioxol, 6-bromo-1-hydroxy-3,4-methylenedioxy-benzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxy-indole, 5,6-dihydroxy-indoline, 5-hydroxy-indole, 6-hydroxy-indole, 7-hydroxy-indole and 2,3-indolindione.

The coupler substances and the developer substances may be contained in the inventive dyeing agent in each case individually or in admixture with one another, the total amount of coupler substances and the developer substances in the inventive dyeing agent in each case being about 0.005 to 20 percent by weight, preferably of about 0.01 to 5 percent by weight and particularly of 0.1 to 2.5 percent by weight, based on the total amount of the dyeing agent, The total amount of the combination of developer substance and coupler substance, contained in the dyeing agent described here, preferably is about 0.01 to 20 percent by weight, an amount of about 0.02 to 10 percent by weight and, in particular, of 0.2 to 6 percent by weight being especially preferred. The developer substances and coupler substances generally are used in about equimolar amounts; however, it is not disadvantageous if the developer substances in this respect are in a different proportion to the coupler substances.

Furthermore, the inventive dyeing agent may additionally contain other dye components, such as 6-amino-2-methylphenol and 2-amino-5-methylphenol, as well as conventional, substantive dyes, for example, triphenylmethane dyes such as 4-[(4'-aminophenyl)-(4'-imino-2",5"-cyclohexadiene-1"-ylidene)-methyl]-2-methylaminobenzene monohydrochloride (C.I. 42 510) and 4-[(4'-amino-3'-methyl-phenyl)-(4"-imino-3"-methyl-2",5"-cyclohexadiene-1"-ylidene)-methyl]-2-methylaminobenzene monohydrochloride (C.I. 42 520), aromatic nitro dyes, such as 4-(2'-hydroxyethyl)amino-nitrotoluene, 2-amino-4,6-dinitrophenol, 2-amino-5-(2'-hydroxyethyl)amino-nitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino-4-nitrobenzene, azo dyes, such as sodium 6-[(4'-aminophenyl)azo]-5-hydroxy-naphthalene-1 sulfonate (C.I. 14 805) and dispersion dyes, such as, for example, 1,4-diaminoanthraquinone and 1,4,5,8-tetraaminoanthraquinone. The dyeing agents may contain these dye components in and amount of about 0.1 to 4 percent by weight.

Of course, the coupler substances and developer substances, as well as the other dye components, if they are bases, can also be used in the form of their physiologically tolerated salts with organic or inorganic acids, such as hydrochloric acid or sulfuric acid, or, if they have aromatic OH groups, in the form of their salts with the bases, for example, as alkali phenolates.

Furthermore, if the dyeing agents are used to dye hair, they may contain further, conventional, cosmetic additives, for example, antioxidants, such as ascorbic acid, thioglycolic acid or sodium sulfite, as well as perfume oils, complexing agents, wetting agents, emulsifiers, thickeners and care materials.

The inventive dyeing agents may be prepared, for example, in the form of a solution, especially an aqueous or aqueous alcoholic solution. However, preparations in the form of a cream, a gel or an emulsion are particularly preferred. Their composition represents a mixture of the dye components with additives, customarily used for such preparations.

Additives, customarily used in solutions, creams, emulsions or gels, are, for example, solvents such as water, low molecular weight aliphatic alcohols, such as ethanol, propanol or isopropanol, glycerin or glycols such as 1,2-propylene glycol, furthermore wetting agents or emulsifies from the classes of anionic, cationic, amphoteric or nonionic surface-active substances, such as fatty alcohol sulfates, ethoxylated fatty alcohol sulfates, alkyl sulfonates, alkylbenzenesulfonates, alkyltrimethylammonium salts, alkyl betaines, ethoxylated fatty alcohols, ethoxylated nonylphenols, fatty acid alkanolamides and ethoxylated fatty esters, furthermore, thickeners such as higher molecular weight fatty alcohols, starch, cellulose derivatives, petrolatum, paraffin oil and fatty acids, as well as, in addition, care materials such as cationic resins, lanolin derivatives, cholesterol, pantothenic acid and betaine. The components mentioned are used in amounts, customary for such purposes; for example, the wetting agents and emulsifies are used in concentrations of about 0.5 to 30 percent by weight, the thickeners in an amount of about 0.1 to 30 percent by weight and the care materials in a concentration of about 0.1 to 5 percent by weight.

Depending on the composition, the inventive dyeing agent may be slightly acidic, neutral or alkaline. In particular, it has a pH of about 6.5 to 11.5, the adjustment to an alkaline value preferably being made with ammonia. However, organic amines, such as monoethanolamine and triethanolamine or also inorganic bases, such as sodium hydroxide and potassium hydroxide, may also be used. For adjusting the pH to an acidic value, inorganic or organic acids, such as phosphoric acid, acetic acid, citric acid or tartaric acid, come into consideration.

If used for the oxidation dyeing of hair, the dyeing agent, described above, is mixed immediately before use with an oxidizing agent. This mixture is applied on the hair in an amount, which is sufficient for the treatment of the hair and depends on the fullness of the hair and generally ranges from about 60 to 200 gram.

As oxidizing agent for developing the dyeing of the hair, mainly hydrogen peroxide or its addition compounds with urea, melamine, sodium borate or sodium carbonate in the form of a 3 percent to 12 percent and preferably 6 percent aqueous solution, but also the oxygen from the air come into consideration. If a 6 percent hydrogen peroxide solution is used as oxidizing agent, the ratio by weight of the dyeing agent to oxidizing agent is 5:1 to 1:2 and preferably, however, 1:1. Larger amounts of oxidizing agent are used especially if the concentration of dye in the hair-dyeing agent is greater or if, at the same time, it is intended to bleach the hair more. The mixture is allowed to react with the hair for about 10 to 45 minutes and preferably for 30 minutes at a temperature of 15° to 50° C. The hair is then rinsed with water and dried. Optionally, after this rinsing, the hair is washed with a shampoo and possibly rinsed with a weak organic acid, such as citric acid or tartaric acid and subsequently dried.

The inventive dyeing agents, containing 1,3-diamino-4-(amino methyl)-benzene derivatives of Formula (I) as coupler substances make it possible to dye hair with excellent color fastness, especially as far as the light fastness, wash fastness and crocking fastness is concerned. With respect to the dyeing properties, the inventive hair-dyeing agent offers a broad range of different color nuances, which depend on the nature and composition of the color components and extend from blond to brown, purple, violet, blue and black color shades. The color shades are distinguished here by their special color intensity. The very good dyeing properties of the dyeing agents of the present application are furthermore distinguished owing to the fact that these agents make it possible to dye keratin fibers, especially human hair, which has not previously been damaged chemically and has turned gray, without any problems and with a good covering power.

The following examples are intended to explain the object of the invention in greater detail, without limiting it.

EXAMPLES

Example 1

Synthesis of 1,3-diamino-4-(aminomethyl)-benzenes (General Synthesis Method)

A. Synthesis of t-butyl (3-t-butoxycarbonylamino-4-formyl-phenyl)-carbamate 2,4-Diamino-benzaldehyde (2.75 g, 0.02 moles) and 8.7 g (0.04 moles) of di-t-butyl dicarbonate are dissolved in a mixture of 50 mL of 2N sodium hydrogen carbonate and 120 mL of acetonitrile. The reaction mixture is stirred for 20 hours. Subsequently, the reaction mixture is poured into water and extracted twice with 100 mL of ethyl acetate. The combined extracts are extracted with dilute hydrochloric acid, then dried with magnesium sulfate and evaporated. The residue subsequently is recrystallized from ethyl acetate.

t-Butyl (3-t-butoxycarbonylamino-4-formyl-phenyl)-carbamate (4.5 g, 67 percent of the theoretical) is obtained.

B. 1,3-Diamino-4-(aminomethyl)-benzene derivatives t-Butyl (3-t-butoxycarbonylamino-4-formyl-phenyl-carbamate (0.033 g, 0.1 mmole) from step A and 0.15 mmole of the corresponding amine are dissolved in 1,2-dichloroethane. Subsequently, 0.1 mL of acetic acid solution (1 M in 1,2-dichloroethane) and 0.06 g (0.3 mmoles) of $NaBH(OAc)_3$ are added and the reaction mixture is stirred for 5 to 15 hours at room temperature. At the end of the reaction, the reaction mixture is poured into 10 mL of ethyl acetate, the organic phase is extracted with sodium hydrogen carbonate and then dried with magnesium sulfate. The solvent is distilled off in a rotary evaporator and the residue purified on silica gel with a 9:1 mixture of petroleum ether and ethyl acetate. The product, so obtained, is heated to 50° C. in 4 mL of ethanol.

Subsequently, to synthesize the hydrochloride, 1.5 mL of a 2.9 molar ethanolic hydrochloric acid solution is added dropwise. The precipitate is filtered off, washed twice with 1 mL of ethanol and then dried.

a. 1,3-Diamino-4-(methylaminomethyl)-benzene hydrochloride
  Amine used: methylamine
  Mass spectrum: $MH^+$ 152 (100)
b. 1.3-Diamino-4-(allylaminomethyl)-benzene hydrochloride
  Amine used: allylamine
  Mass spectrum: $MH^+$ 178 (100)
c. 2-(2,4-Diaminobenzylamino)-ethanol hydrochloride
  Amine used: ethanolamine
  Mass spectrum: $MH^+$ 182 (100)
d. 1,3-Diamino-4-(pyrrolidine-1-ylmethyl)-benzene hydrochloride
  Amine used: pyrrolidine
  Mass spectrum: $MH^+$ 192 (100)
e. 1-(2,4-Diaminobenzyl)-pyrrolidine-3-ol hydrochloride
  Amine used: 3-pyrrolidinol
  Mass spectrum: $MH^+$ 208 (100)
f. [1-(2,4-Diaminobenzyl)-pyrrolidine-2-yl]-methanol hydrochloride
  Amine used: prolinol
  Mass spectrum: $MH^+$ 222 (100)
g. 1,3-Diamino-4-[(2-amino-ethylamino)-methyl]-benzene hydrochloride
  Amine used: ethylenediamine
  Mass spectrum: $MH^+$ 181 (100)
h. 1,3-Diamino-4-(morpholine-4-ylmethyl)-benzene hydrochloride
  Amine used: morpholine
  Mass spectrum: $MH^+$ 208 (100)
i. 1-(2,4-Diaminobenzyl)-piperidine-4-ol hydrochloride
  Amine used: 4-hydroxy-piperidine
  Mass spectrum: $MH^+$ 222 (100)
j. 1-(2,4-diamino-benzyl)-piperidine-3-ol hydrochloride
  Amine used: 3-hydroxy-piperidine
  Mass spectrum: $MH^+$ 222 (100)
k. N-[2-(2,4-diaminobenzylamino)-ethyl]-acetamide hydrochloride
  Amine used: N-acetyl-ethylenediamine
  Mass spectrum: $MH^+$ 223 (100)
l. 1,3-Diamino-4-[(2-methoxyethylamino)-methyl]-benzene hydrochloride
  Amine used: 2-methoxyethylamine
  Mass spectrum: $MH^+$ 196 (100)
m. 2-(2,4-Diaminobenzylamino)-propane-1-ol hydrochloride
  Amine used: 2-amino-propanol
  Mass spectrum: $MH^+$ 196 (100)
n. 1,3-Diamino-4-{[(tetrahydrofuran-2-ylmethyl)-amino]-methyl}-benzene hydrochloride
  Amine used: tetrahydrofurfurylamine
  Mass spectrum: $MH^+$ 222 (100)

Examples 2 to 15

Hair Dyeing Agent

Hair-dyeing solutions of the following composition are prepared:

| | |
|---|---|
| 1.25 mmoles | developer substance of Formula (I) of Table 1 |
| 1.25 mmoles | coupler substance of Table 1 |
| 1.0 g | potassium oleate (8% aqueous solution) |
| 1.0 g | ammonia (22% aqueous solution) |
| 1.0 g | ethanol |
| 0.3 g | ascorbic acid |
| ad 100.0 g | water |

Immediately before use, 50 g of the above dye solution are mixed with 50 g of a 6 percent aqueous hydrogen peroxide solution. Subsequently, the mixture is applied on bleached hair. After a period of action of 30 minutes at 40° C., the hair is rinsed with water, washed with a conventional, commercial shampoo and dried. The resulting dyeings are summarized in Table 1.

TABLE 1

| | | Coupler Substance | | | |
|---|---|---|---|---|---|
| Example No. | Coupler Substance of Formula (I) | I. 1,4-diamino benzene | II. 2,5-diamino-toluene sulfate | III. 2,5-diaminophenyl-ethanol sulfate | IV. 4,5-diamino-1-(2'-hydroxyethyl)-pyrazole sulfate |
| 2. | of Example 1a | dark blue | dark blue | dark blue | purple |
| 3. | of Example 1b | dark blue | dark blue | dark blue | purple |
| 4. | of Example 1c | dark blue | dark blue | dark blue | purple |
| 5. | of Example 1d | dark blue | blue | dark blue | purple |
| 6. | of Example 1e | dark blue | dark blue | dark blue | purple |
| 7. | of Example 1f | dark blue | dark blue | dark blue | purple |
| 8. | of Example 1g | dark blue | dark blue | blue | purple |
| 9. | of Example 1h | dark blue | dark blue | blue | purple |
| 10. | of Example 1i | dark blue | blue | blue | purple |
| 11. | of Example 1j | dark blue | blue | blue | purple |
| 12. | of Example 1k | dark blue | blue | blue | purple |
| 13. | of Example 1l | dark blue | blue | blue | purple |
| 14. | of Example 1m | dark blue | blue | blue | purple |
| 15. | of Example 1n | dark blue | blue | blue | purple |

Examples 16 to 27

Hair Dyeing Agent

Hair-dyeing solutions of the following composition are prepared:

| | |
|---|---|
| X g | 1,3-diamino-4-(aminomethyl)-benzene derivative of Formula (I) (coupler substance K1 to K3 of Table 3) |
| U g | developer substance E1 to E7 of Table 2 |
| Y g | coupler substance K4 to K15 of Table 3 |
| 10.0 g | potassium oleate (8% aqueous solution) |
| 10.0 g | ammonia (22% aqueous solution) |
| 10.0 g | ethanol |
| 0.3 g | ascorbic acid |
| ad 100.0 g | water |

Immediately before use, 30 g of the above dye solution are mixed with 30 g of a 6 percent aqueous hydrogen peroxide solution. Subsequently, the mixture is applied on bleached hair. After a period of action of 30 minutes at 40° C., the hair is rinsed with water, washed with a conventional, commercial shampoo and dried. The resulting dyeings are summarized in Table 5.

Examples 28 to 39

Hair Dyeing Agents

Creamy hair-dyeing compositions of the following composition are prepared:

| | |
|---|---|
| X g | 1,3-diamino-4-(aminomethyl)-benzene derivative of Formula (I) (coupling substance K1 to K3 of Table 3) |
| U g | developer substance E1 to E7 of Table 2 |
| Y g | coupling substance K4 to K15 of Table 3 |
| Z g | substantive dye D1 to D3 of Table 4 |
| 15.0 g | cetyl alcohol |
| 0.3 g | ascorbic acid |
| 3.5 g | sodium lauryl alcohol diglycol ether sulfate (28% aqueous solution) |
| 3.0 g | ammonia (22% aqueous solution) |
| 0.3 g | sodium sulfite, water-free |
| ad 100.0 g | water |

Immediately before use, 30 g of the above dye solution are mixed with 30 g of a 6 percent aqueous hydrogen peroxide solution. Subsequently, the mixture is applied on bleached hair. After a period of action of 30 minutes at 40° C., the hair is rinsed with water, washed with a conventional, commercial shampoo and dried. The resulting dyeings are summarized in Table 6.

Unless stated otherwise, all percentages, given in the application above, are percentages by weight.

TABLE 2

| Developer Substances | |
|---|---|
| E1 | 1,4-diaminobenzene |
| E2 | 2-(2,5-diamino-phenyl)-ethanol sulfate |
| E3 | 4-amino-3-methyl-phenol |
| E4 | 4-aminophenol |
| E5 | N,N-bis(2-hydroxyethyl)-p-phenylenediamine |
| E6 | 4,5-diamino-1-(2-hydroxyethyl)-pyrazole sulfate |
| E7 | 2,5-diaminotoluene sulfate |

TABLE 3

| Coupler Substances | |
|---|---|
| K1 | 1,3-diamino-4-(allylaminomethyl)-benzene hydrochloride |
| K2 | 2-(2,4-diaminobenzylamino)-ethanol hydrochloride |
| K3 | 1,3-diamino-4-[(2-aminoethylamino)-methyl]-benzene hydrochloride |
| K4 | 2-amino-4-(2'-hydroxyethyl)amino-anisole sulfate |

TABLE 3-continued

Coupler Substances

| | |
|---|---|
| K5 | 1,3-diamino-4-(2'-hydroxyethoxy)benzene sulfate |
| K6 | 1,3-bis(2,4-diaminophenoxy)propane tetrahydrochloride |
| K7 | 3-amino-phenol |
| K8 | 5-amino-2-methyl-phenol |
| K9 | 3-amino-2-chloro-6-methyl-phenol |
| K10 | 5-amino-4-fluoro-2-methyl-phenol sulfate |
| K11 | 1-naphthol |
| K12 | 2-amino-5-methylphenol |
| K13 | 1,3-dihydroxy-benzene |
| K14 | 2-methyl-1,3-dihydroxy-benzene |
| K15 | 1-chloro-2,4-dihydroxy-benzene |

TABLE 4

Direct Dyes

| | |
|---|---|
| D1 | 2,6-diamino-3-((pyridine-3-yl)azo)pyridine |
| D2 | 6-chloro-2-ethylamino-4-nitrophenol |
| D3 | 2-amino-6-chloro-4-nitrophenol |

TABLE 5

Hair Dyeing Agents

| Dye | 16 | 17 | 18 | 19 | 20 | 21 |
|---|---|---|---|---|---|---|
| | (amount of dye in grams) | | | | | |
| K1 | 0.10 | | 0.05 | | 0.10 | 0.12 |
| K2 | | 0.12 | | 0.07 | | |
| E1 | 0.30 | | | | | |
| E2 | | | | | 0.25 | 0.30 |
| E7 | | 0.25 | 0.30 | 0.25 | | |
| K4 | | | 0.03 | | | |
| K5 | | | | 0.05 | | |
| K6 | | | | 0.05 | | |
| K7 | 0.05 | | | | | |
| K8 | | 0.05 | | | | |
| K9 | | | 0.05 | 0.10 | 0.10 | 0.10 |
| K12 | | | 0.05 | | | 0.05 |
| K13 | 0.20 | | | 0.15 | 0.20 | 0.10 |
| K14 | | 0.20 | | 0.10 | | 0.10 |
| K15 | | | 0.20 | | | |
| Dyeing Result | blond | blond | blond | blond | blond | blond |

| Dye | 22 | 23 | 24 | 25 | 26 | 27 |
|---|---|---|---|---|---|---|
| | (amount of dye in grams) | | | | | |
| K3 | 0.10 | 0.12 | 0.05 | 0.07 | 0.10 | 0.12 |
| E1 | 0.30 | | | | | |
| E2 | | | 0.20 | | 0.20 | 0.30 |
| E3 | | | 0.10 | | | |
| E4 | | | 0.05 | | | |
| E5 | | | | 0.03 | | |
| E6 | | | | 0.10 | | |
| E7 | | 0.25 | 0.05 | 0.25 | | |
| K4 | | | 0.05 | | | |
| K5 | | | | 0.05 | | |
| K6 | | | | | | |
| K7 | 0.05 | | 0.05 | | | |
| K8 | | 0.05 | | | | |
| K9 | | | 0.05 | 0.10 | 0.10 | 0.10 |
| K10 | | | | | 0.05 | |
| K11 | | | | 0.05 | | |
| K12 | | 0.30 | | | | |
| K13 | 0.20 | | | 0.15 | 0.20 | 0.10 |
| K14 | | 0.20 | | 0.10 | | 0.10 |
| K15 | | | 0.20 | | | |

TABLE 5-continued

Hair Dyeing Agents

| Dyeing Result | blond | blond | rose | blond | blond-rose | blond |
|---|---|---|---|---|---|---|

TABLE 6

Hair Dyeing Agents

| Dye | 28 | 29 | 30 | 31 | 32 | 33 |
|---|---|---|---|---|---|---|
| | (amount of dye in grams) | | | | | |
| K1 | 0.60 | 1.30 | 0.80 | 0.15 | | 0.15 |
| K2 | | | 0.15 | | 0.15 | |
| K3 | | | 0.20 | | | |
| E1 | 1.00 | | | | | |
| E2 | 0.20 | | | | | |
| E3 | | | | | 0.10 | |
| E4 | | | | 0.05 | | |
| E5 | | 1.60 | | | | 0.70 |
| E6 | | | | | | 0.20 |
| E7 | | | 1.80 | 0.70 | 0.70 | |
| K4 | 0.60 | | | | | |
| K8 | | | | | | 0.05 |
| K9 | | | 0.05 | 0.10 | 0.10 | 0.10 |
| K10 | | | | | | 0.05 |
| K11 | | | | | | 0.05 |
| K12 | | 0.10 | 0.05 | | | |
| K13 | 1.10 | 1.10 | 1.10 | 0.40 | 0.40 | 0.40 |
| K14 | | | | | | |
| K15 | | | | | | |
| D1 | | | | | | 0.05 |
| D2 | | | | 0.10 | 0.10 | 0.10 |
| D3 | | | | | | 0.05 |
| Dyeing Result | black | black | black | brown | brown | brown |

| Dye | 34 | 35 | 36 | 37 | 38 | 39 |
|---|---|---|---|---|---|---|
| | (amount of dye in grams) | | | | | |
| K3 | 0.60 | 1.30 | 1.15 | 0.15 | 0.15 | 0.15 |
| E1 | 1.50 | | | | | |
| E2 | | | 0.80 | | | |
| E5 | | 1.60 | | | | 0.70 |
| E7 | | | 1.80 | | 0.70 | |
| K4 | 0.60 | | | | | |
| K9 | | | 0.05 | 0.10 | 0.10 | 0.10 |
| K13 | 1.10 | 1.10 | 1.10 | 0.40 | 0.40 | 0.40 |
| D2 | | | | 0.10 | 0.10 | |
| D3 | | | | 0.10 | | |
| Dyeing Result | black | black | black | brown | brown | brown |

What is claimed is:

1. A 1,3-diamino-4-(aminomethyl)-benzene derivative compound of the formula (I), or a physiologically tolerated, water-soluble salt thereof:

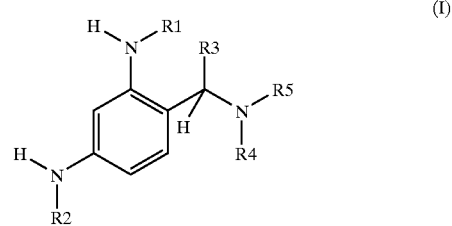

(I)

wherein R1 and R2, independently of one another, each represent hydrogen, a $C_1$–$C_6$ alkyl group, a $C_2$–$C_4$ hydroxyalkyl group or a $C_3$–$C_4$ dihydroxyalkyl group, R3 is hydrogen or a $C_1$–$C_4$ alkyl group, R4 and R5, independently of one another, each represent hydrogen, a $C_1$–$C_2$ alkoxy group, a saturated $C_1$–$C_6$ alkyl group, an unsaturated $C_3$–$C_6$ alkyl group, a $C_2$–$C_4$ hydroxyalkyl group, a $C_3$–$C_4$ dihydroxyalkyl group, a $C_2$–$C_4$ amino alkyl group, a $C_2$–$C_4$ dimethylamino alkyl group, a $C_2$–$C_4$ acetylamino alkyl group, a $C_2$–$C_4$ methoxyalkyl group, a $C_2$–$C_4$ ethoxyalkyl group, a $C_1$–$C_4$ cyanalkyl group, a $C_1$–$C_4$ carboxy alkyl group, a $C_1$–$C_4$ aminocarbonylalkyl group, a pyridyl methyl group, a furfuryl group, a thienyl methyl group, a substituted pyridyl group or a group of formula (II)

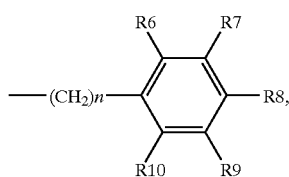

(II)

or R4 and R5 together with N form a ring of formula

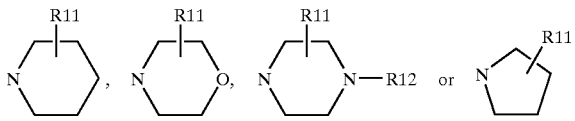

wherein R6, R7, R8, R9 and R10, independently of one another, each represent hydrogen, a halogen atom, a cyano group, a hydroxy group, a $C_1$–$C_4$ alkoxy group, a $C_2$–$C_4$ hydroxyalkoxy group, a $C_1$–$C_6$ alkyl group, a $C_1$–$C_4$ alkyl thioether group, a mercapto group, a nitro group, an amino group, an alkylamino group, a di($C_1$–$C_6$ alkyl)amino group, a dihydroxy-($C_3$–$C_4$)alkyl)amino group, a di($C_1$–$C_4$ hydroxyalkyl)amino group, a ($C_1$–$C_4$ hydroxyalkyl)-($C_1$–$C_6$ alkyl)-amino group, a trifluoromethane group, a —C(O)H group, a —C(O)CH$_3$ group, a —C(O)CF$_8$ group, a —Si(CH$_3$)$_3$ group, a $C_1$–$C_4$ hydroxyalkyl group, a $C_2$–$C_4$ dihydroxyalkyl group, a carboxy group or a pyrrolidine group or two adjacent ones of said R6 to R10 form an —O—CH$_2$—O— link, R11 is hydrogen, a hydroxy group, a carboxy group, an amino-carbonyl group or a hydroxymethyl group;

R12 is hydrogen or a $C_1$–$C_6$ alkyl group; and n is 0 or 1;

with the proviso that at least one of said R1 to R5 groups is not hydrogen.

2. An agent for oxidative dyeing of keratin fibers containing at least one coupler substance and at least one developer substance, wherein said at least one coupler substance comprises at least one 1,3-diamino-4-(aminomethyl)-benzene derivative compound of the formula (I) or a physiologically tolerated, water-soluble salt thereof;

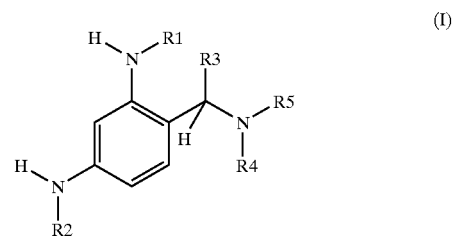

(I)

wherein R1 and R2, independently of one another, each represent hydrogen, a $C_1$–$C_6$ alkyl group, a $C_2$–$C_4$ hydroxyalkyl group or a $C_3$–$C_4$ dihydroxyalkyl group, R3 is hydrogen or a $C_1$–$C_4$ alkyl group, R4 and R5, independently of one another, each represent hydrogen, a $C_1$–$C_2$ alkoxy group, a saturated $C_1$–$C_8$ alkyl group, an unsaturated $C_3$–$C_6$ alkyl group, a $C_2$–$C_4$ hydroxyalkyl group, a $C_3$–$C_4$ dihydroxyalkyl group, a $C_2$–$C_4$ amino alkyl group, a $C_2$–$C_4$ dimethylamino alkyl group, a $C_2$–$C_4$ acetylamino alkyl group, a $C_2$–$C_4$ methoxy alkyl group, a $C_2$–$C_4$ ethoxy alkyl group, a $C_1$–$C_4$ cyanalkyl group, a $C_1$–$C_4$ carboxyalkyl group, a $C_1$–$C_4$ aminocarbonyl alkyl group, a pyridyl methyl group, a furfuryl group, a thienyl methyl group, a substituted pyridyl group or a group of formula (II)

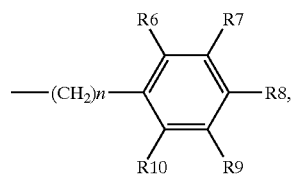

(II)

or R4 and R5 together with N form a ring of formula

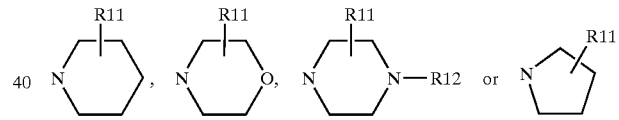

wherein R6, R7, R8, R9 and R10, independently of one another, each represent hydrogen, a halogen atom, a cyano group, a hydroxy group, a $C_1$–$C_4$ alkoxy group, a $C_2$–$C_4$ hydroxyalkoxy group, a $C_1$–$C_6$ alkyl group, a $C_1$–$C_4$ alkyl thioether group, a mercapto group, a nitro group, an amino group, an alkylamino group, a di($C_1$–$C_6$ alkyl)amino group, a (dihydroxy($C_3$–$C_4$)alkyl)amino group, a di($C_1$–$C_4$ hydroxyalkyl)amino group, a ($C_1$–$C_4$ hydroxyalkyl)-($C_1$–$C_6$ alkyl)amino group, a trifluoromethane group, a —C(O)H group, a —C(O)CH$_3$ group, a —C(O)CF$_3$ group, a —Si(CH$_3$)$_3$ group, a $C_1$–$C_4$ hydroxyalkyl group, a $C_2$–$C_4$ dihydroxyalkyl group, a carboxy group or a pyrrolidine group or two adjacent ones of said R6 to R10 form an —O—CH$_2$—O link, R11 is hydrogen, a hydroxy group, a carboxy group, an amino carbonyl group or a hydroxy methyl group;

R12 is hydrogen or a $C_1$–$C_6$ alkyl group; and n is 0 or 1;

with the proviso that at least one of said R1 to R5 groups is not hydrogen.

3. The agent as defined in claim 2, wherein at least one of said R1, R2 and R3 is hydrogen.

4. The agent as defined in claim 2, wherein one of said R4 and R5 is a $C_2$–$C_6$ hydroxyalkyl group, an unsaturated $C_3$–$C_6$ alkyl group, a $C_2$–$C_4$ aminoalkyl group or a $C_1$–$C_4$ alkyl group.

5. The agent as defined in claim 2, wherein said at least one 1,3-diamino-4-(aminomethyl)-benzene derivative compound is 1,3-diamino-4-(methylaminomethyl)benzene, 1,3-diamino-(4-allylaminomethyl)-benzene, 2-(2,4-diamino-benzylamino)-ethanol or 1,3-diamino-4-((2-aminoethylamino)-methyl)-benzene.

6. The agent as defined in claim 2, containing from 0.005 to 20 percent by weight of said at least one 1,3-diamino-4-(aminomethyl)-benzene derivative compound.

7. The agent as defined in claim 2, wherein the at least one developer substance is selected from the group consisting of 1,4-diamino-benzene, 1,4-diamino-2-methylbenzene, 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophene-2-yl)-benzene, 1,4-diamino-2-(thiophene-3-yl)-benzene, 1,4-diamino-2-(pyridine-3-yl)-benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)-benzene, 2-(2-acetylamino)ethoxy)-1,4-diaminobenzene, 4-phenylaminoaniline, 4-dimethylamino-aniline, 4-diethyl-aminoaniline, 4-dipropylaminoaniline, 4-[ethyl(2-hydroxyethyl)amino]aniline, 4-[di(2-hydroxyethyl)amino]-aniline, 4-[di(2-hydroxyethyl)-amino]-2-methyl-aniline, 4-[(2-methoxyethyl)amino]-aniline, 4-[(3-hydroxy-propyl)amino]aniline, 4-[(2,3-dihydroxypropyl)amino]-aniline, 1,4-diamino-2-(1-hydroxyethyl)benzene, 1,4-diamino-2-(2-hydroxyethyl)-benzene, 1,4-diamino-2-(1-methylethyl) benzene, 1,3-bis[(4-aminophenyl)(2-hydroxyethyl)amino]-2-propanol, 1,4-bis[(4-amino-phenyl)amino]-butane, 1,8-bis(2,5-diaminophenoxy)-3,6-dioxaoctane, 4-amino-phenol, 4-amino-3-methyl-phenol, 4-amino-3-(hydroxymethyl)-phenol, 4-amino-3-fluorophenol, 4-methylaminophenol, 4-amino-2-(aminomethyl)-phenol, 4-amino-2-(hydroxymethyl)-phenol, 4-amino-2-fluoro-phenol, 4-amino-2-[(2-hydroxyethyl)-amino]methyl-phenol, 4-amino-2-methyl-phenol, 4-amino-2-(methoxymethyl)-phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol and 1,2,4-trihydroxybenzene.

8. The agent as defined in claim 2, wherein said at least one coupler substance includes at least one member selected from the group consisting of N-(3-dimethylamino-phenyl) urea, 2,6-diaminopyridine, 2-amino-4-[(2-hydroxyethyl) amino]anisole, 2,4-diamino-1-fluoro-5-methylbenzene, 2,4-diamino-1-methoxy-5-methylbenzene, 2,4-diamino-1-ethoxy-5-methyl-benzene, 2,4-diamino-1-(2-hydroxyethoxy)-5-methylbenzene, 2,4-di[(2-hydroxy-ethyl)amino]-1,5-dimethoxybenzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxy-pyridine, 1,3-diaminobenzene, 2,4-diamino-1-(2-hydroxyethoxy)-benzene, 1,3-diamino-4-(2,3-dihydroxypropoxy)-benzene, 1,3-diamino-4-(3-hydroxypropoxy)-benzene, 1,3-diamino-4-(2-methoxyethoxy)-benzene, 2,4-diamino-1,5-di(2-hydroxyethoxy)-benzene, 1-(2-aminoethoxy)-2,4-diaminobenzene, 2-amino-1-(2-hydroxyethoxy)-4-methylamino-benzene, 2,4-diamino-phenoxyacetic acid, 3-[di(2-hydroxyethyl)amino]-aniline, 4-amino-2-di[(2-hydroxyethyl)amino]-1-ethoxy-benzene, 5-methyl-2-(1-methylethyl)-phenol, 3-[(2-hydroxyethyl)amino]-aniline, 3-[(2-aminoethyl)amino]-aniline, 1,3-di(2,4-diaminophenoxy)-propane, di(2,4-diaminophenoxy)-methane, 1,3-diamino-2,4-dimethoxy-benzene, 2,6-bis-(2-hydroxyethyl)aminotoluene, 4-hydroxyindole, 3-dimethylamino-phenol, 3-diethylamino-phenol, 5-amino-2-methylphenol, 5-amino-4-fluoro-2-methyl-phenol, 5-amino-4-methoxy-2-methyl-phenol, 5-amino-4-ethoxy-2-methyl-phenol, 3-amino-2,4-dichlorophenol, 5-amino-2,4-dichloro-phenol, 3-amino-2-methyl-phenol, 3-amino-2-chloro-6-methylphenol, 3-amino-phenol, 2-[(3-hydroxyphenyl)-amino]acetamide, 5-[(2-hydroxyethyl) amino]-4-methoxy-2-methyl-phenol, 5[(2-hydroxyethyl)-amino]-2-methylphenol, 3-[(2-hydroxyethyl)amino]-phenol, 3-[(2-methoxyethyl)-amino]-phenol, 5-amino-2-ethyl-phenol, 5-amino-2-methoxy-phenol, 2-(4-amino-2-hydroxyphenoxy)ethanol, 5-[(3-hydroxypropyl)amino]-2-methylphenol, 3-[(2,3-dihydroxypropyl)-amino]-2-methylphenol, 3-[(2-hydroxyethyl)amino]-2-methyl-phenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxy-naphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxy-phenol, 3,4-methylene-dioxy-aniline, 5-[(2-hydroxyethyl)amino]-1, 3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxy-indole, 6-hydroxyindole, 7-hydroxyindole and 2,3-indolindione.

9. The agent as defined in claim 2, containing a total amount of 0.005 to 20 percent by weight of said at least one developer substance and said at least one coupler substance.

10. The agent as defined in claim 2, further comprising at least one substantive dye.

11. The agent as defined in claim 2, having a pH of 6.5 to 11.5.

12. The agent as defined in claim 2, consisting of a hair-dyeing agent.

* * * * *